United States Patent [19]
Herleikson

[11] Patent Number: 5,357,969
[45] Date of Patent: Oct. 25, 1994

[54] METHOD AND APPARATUS FOR ACCURATELY DISPLAYING AN ECG SIGNAL

[75] Inventor: Earl C. Herleikson, Groton, Mass.

[73] Assignee: Hewlett-Packard Company, Palo Alto, Calif.

[21] Appl. No.: 32,895

[22] Filed: Mar. 18, 1993

[51] Int. Cl.⁵ ............................................. A61B 5/04
[52] U.S. Cl. ............................................. 128/696
[58] Field of Search ............................... 128/696

[56] References Cited

U.S. PATENT DOCUMENTS

| 3,569,852 | 3/1971 | Berkovits | 128/696 |
| 4,381,786 | 5/1983 | Duggan | 128/696 |
| 4,408,615 | 10/1983 | Grossman | 128/696 |
| 4,494,551 | 1/1985 | Little et al. | 128/696 |

Primary Examiner—William E. Kamm
Attorney, Agent, or Firm—Brent F. Logan; Curtis G. Rose

[57] ABSTRACT

Method and apparatus for removing baseline wander from an ECG signal. The ECG signal is filtered with a high-pass filter having a variable corner frequency. In response to finding low-frequency components in the output of the high-pass filter, its corner frequency is temporarily increased. The corner frequency may decrease according to a decay function or sensing the absence of a low-frequency component in the filter's output. The corner frequency may be decreased in response to sensing ECG activity.

8 Claims, 6 Drawing Sheets

METHOD AND APPARATUS FOR ACCURATELY DISPLAYING AN ECG SIGNAL

BACKGROUND OF THE INVENTION

An electrocardiogram (ECG) measurement consists of measuring a small, approximately 5 milli-Volt, signal produced by the heart superimposed upon a relatively large, approximately 300 mV, low-frequency potential produced by the skin-to-electrode interface. The large low-frequency potential is called baseline wander. It is desirable to remove the baseline wander without altering the ECG signal.

The American Association of Medical Instrumentation (AAMI) has specified two cases for the removal of the electrode offset. The first specification is for the case of ECG monitors. In this case, it is more important for the ECG signal to remain visible on the screen than to make a diagnosis based on the precise measurements of the ECG waveform. Thus, the monitor specification requires the frequency response to be only as low as 0.5 Hz. The most typical filter for an ECG monitor is a single pole high pass filter having a 3 dB corner of 0.5 Hz.

The second specification is for the case of diagnostic ECG measurement. This specification requires a passband down to 0.05 Hz so the high pass filter causes only minimal distortion of the ECG signal. This maintains a high degree of accuracy allowing for the diagnosis of a heart.

Typically, the distortion that is created by a single-pole high-pass filter is due to its nonlinear time delay. A single-pole 0.5 Hz high-pass filter can be greatly improved by giving it constant delay. Alternatively, the corner frequency can be decreased, increasing the filter's susceptibility to baseline wander.

The effect of nonlinear time-delay distortion on the diagnosis of an ECG signal is most pronounced with respect to a calculation of ST segment elevation or depression. This calculation is based on the difference in voltage from the PQ segment just before the QRS and voltage of the ST segment just after the QRS. Solutions to this problem have in the past consisted of either decreasing the frequency of the high pass filter as shown by the AAMI specification of diagnostic ECG instrumentation for 0.05 Hz, or adding a minimum of 2 seconds of delay in order to perform a constant delay 0.5 Hz high pass.

For the foregoing reasons, there is a need for an ECG high-pass filter which has decreased susceptibility to baseline wander, yet provides an accurate representation of the input ECG signal for monitor and diagnostic purposes.

SUMMARY OF THE INVENTION

The present invention is directed to method and apparatus which dynamically varies the corner frequency of an ECG high-pass filter, allowing it to increase and thus effectively minimize the effects of baseline wander, yet detect periods of ECG activity and, in response, decrease for maximum accuracy, thereby satisfying this need.

In order to have a real-time display in a defibrillator-monitor application yet also minimize the distortion, the invention comprises a variable high pass filter. Two controls vary the frequency of the high pass filter. One control responds to the activity of the ECG signals to dramatically lower the frequency of the filter during a QRS event in the ECG. By not responding to the QRS part of the waveform, the "tail" produced by the energy of the QRS complex is virtually eliminated, yet good removal of the baseline wander is achieved during the rest of the waveform. The other control responds to the DC offset of the output of the filter. By responding to the DC level at the output of the filter, the bandwidth of the filter can be reduced when there is very little baseline wander and the signal is very stable. This further reduces the possibility of distortion on the other parts of the waveform such as the T waves, which are broader and are not high enough in activity to shut down the bandwidth.

These two methods for dynamically varying the frequency of the high pass filter, provide the best solution for keeping the ECG trace on screen for the operator to see with minimal processing delay and minimal ECG distortion.

DETAILED DESCRIPTION OF THE INVENTION

Figure 1:
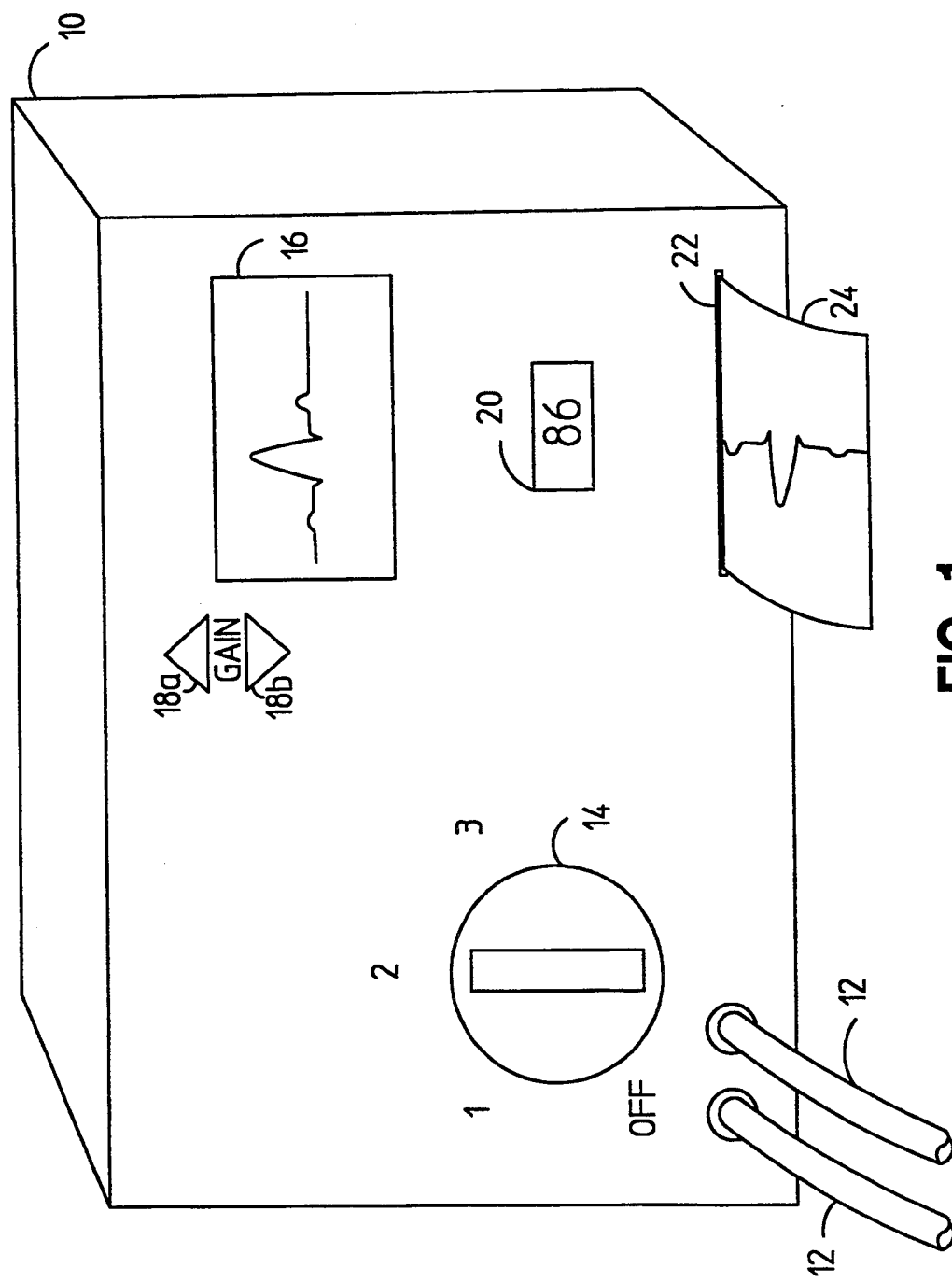
FIG. 1 shows a perspective view of a defibrillator-monitor.

Referring now to the drawings, FIG. 1 shows a defibrillator 10. The defibrillator delivers an electrical impulse to a patient via cables 12 and paddles (not shown).

The defibrillator 10 has a switch 14 for selecting the amount of energy to be delivered to the patient. Switches for initiating the discharge are typically located on the paddles.

The defibrillator 10 has a display 16 for showing the patient's heart waveform, enabling the operator to diagnose the patient's condition. Gain switches 18a, 18b enable the operator to increase or decrease the vertical size of the heart waveform on the display 16. A heart rate display 20 shows the patient's current heart rate.

The defibrillator 10 also has a strip recorder 22 for printing ECG waveforms in permanent form on paper strips 24.

Figure 2:
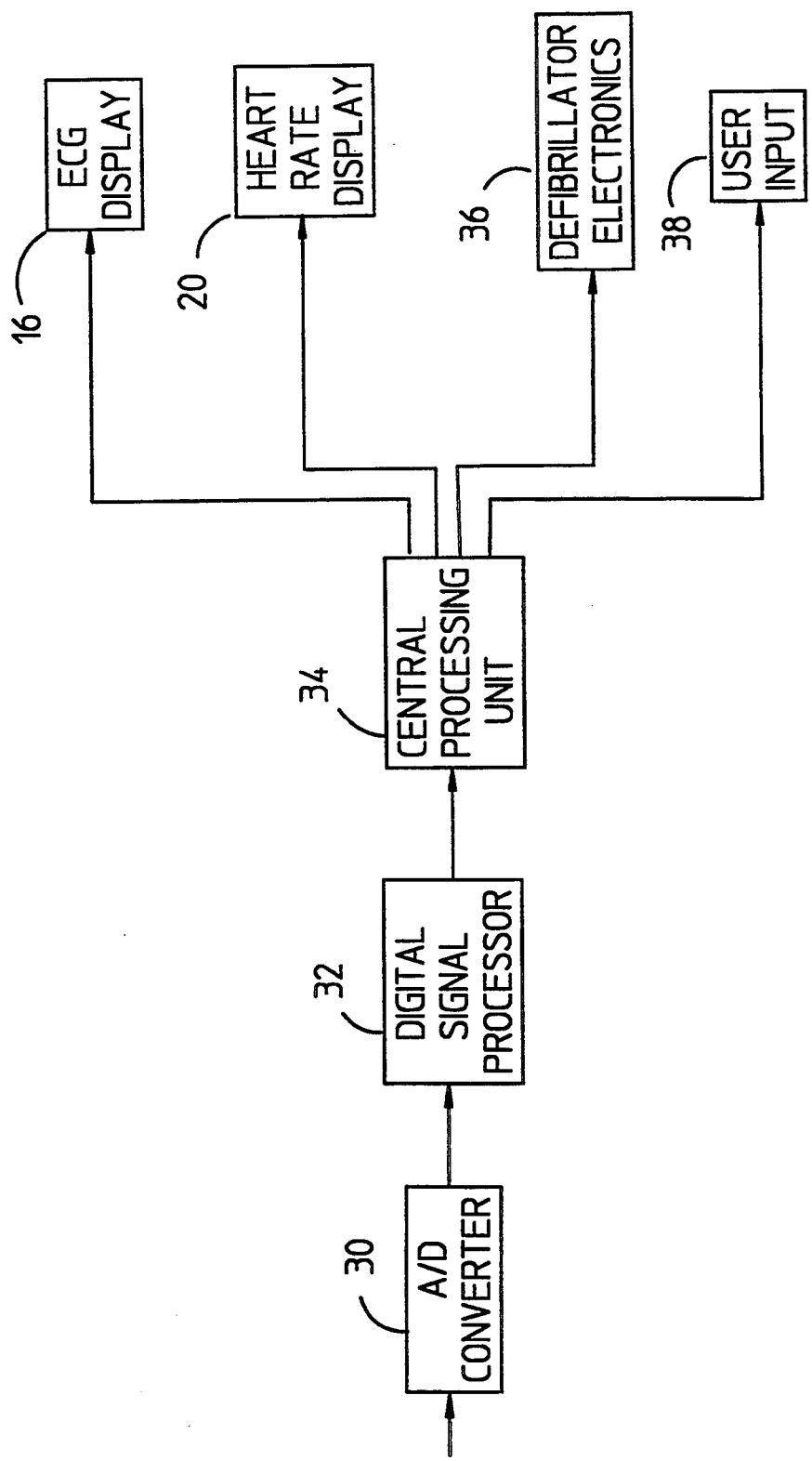
FIG. 2 shows a general block diagram of a defibrillator including the present invention.

Referring now to FIG. 2, the defibrillator 10 provides the ECG signals received by the paddles and transmitted on the cables 12 to an analog to digital (A/D) converter 30. Alternatively, the ECG signals may come from a standard patient lead set acquire by separate electrodes. The output of the A/D converter is provided to a digital signal processor 32 which filters the digital ECG signals and provides them to a central processing unit 34.

The central processing unit 34 displays an ECG representation of the ECG data on the ECG display 16 and displays the patient's heart rate on the heart rate display 20. The central processing unit also controls the defibrillator electronics 36.

The central processing unit 34 also accepts input from the user switches 38, including the energy selection switch 14, the discharge switches (not shown) and the gain switches 18a and 18b.

The digital signal processor 32 performs many functions on the digitized ECG signals, including low-pass and high-pass filtering, slope detection, activity detection, peak detection, and attenuation. Basic to the present invention is the digital signal processor's function of providing a high-pass variable-corner-frequency filter. The basic building block of a real-time variable ECG high-pass filter is a single-pole digital filter.

The output y[0] at time t=0 of a digital high-pass filter is equal to its input x[0] at the same time less an accumulated amount w[0] which tracks the DC offset.

$$y[0] = x[0] - w[0] \tag{1}$$

The accumulated amount w[0] is equal to the accumulated amount at the previous time w[−1] plus some fraction "a" of the previous difference between the accumulated amount and the input. That is, $$w[0] = w[-1] + a(x[-1] - w[-1]) \tag{2}$$

which simplifies to $$w[0] = w[-1] + ay[-1]. \tag{3}$$

The fraction, or coefficient, "a" determines the frequency response or time constant $\tau$ of the filter according to the equation:

$$\tau = \frac{1}{aF_s} \tag{4}$$

where $F_s$ is the sampling frequency. For example, if Fs=1000 Hz, and a =1/1000, then the time constant t would be 1 second and the 3 dB frequency $F_c$ (in Hertz) of the filter would be $$F_c = \frac{1}{2\pi\tau}. \tag{5}$$

By dynamically changing coefficient "a", the responsiveness of the filter can be changed.

A single-pole low-pass digital filter is very similar to the high-pass filter just described. Its output is the accumulated amount w[0], rather than y[0].

Figure 3:
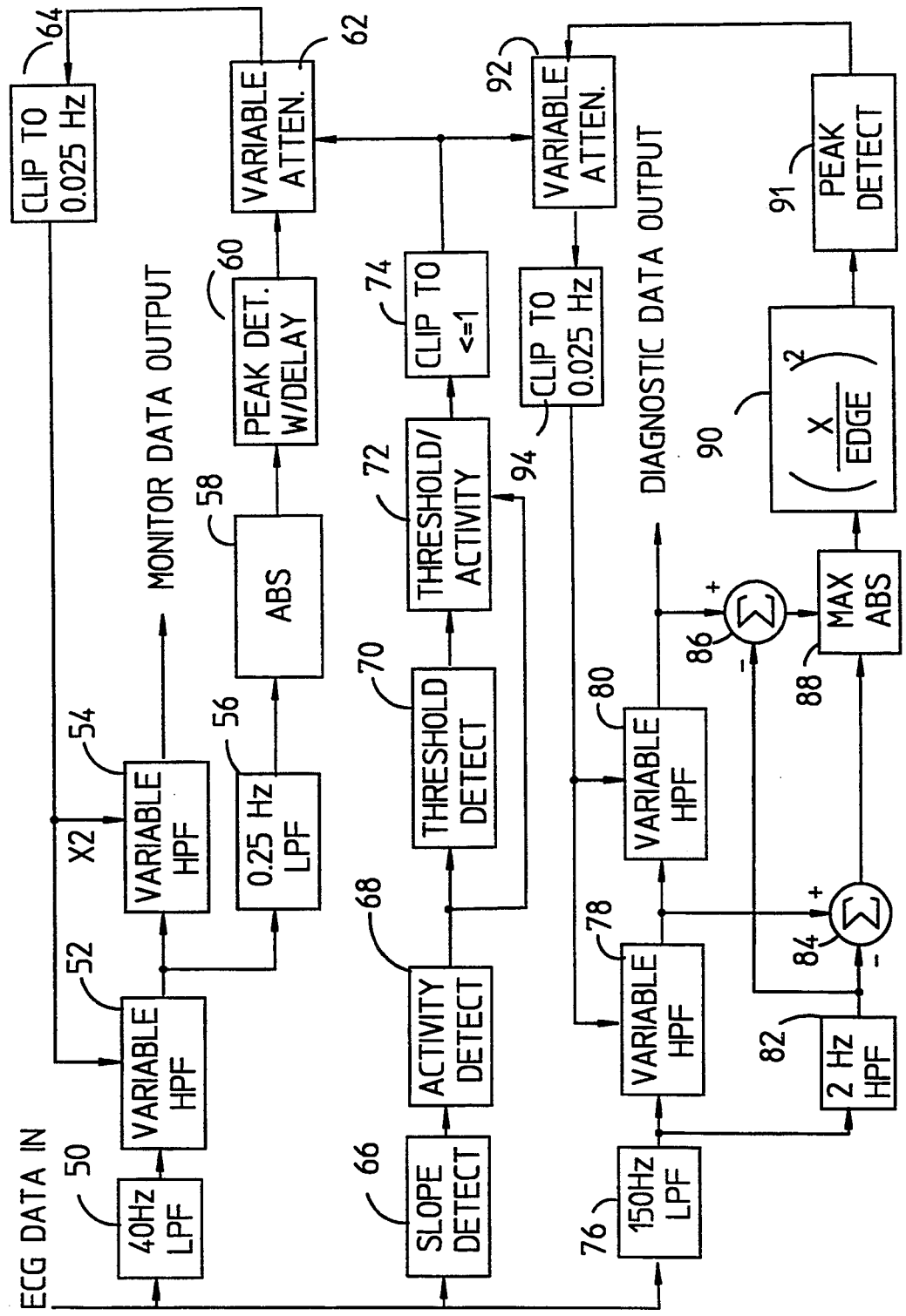
FIG. 3 shows a detailed block diagram of a portion of the general block diagram of FIG. 2.

Referring now to FIG. 3, a detailed block diagram of a real-time variable ECG high-pass filter can be seen. Sampled ECG data is provided to a 40 Hz low-pass filter 50, a 150 Hz low-pass filter 76, and a slope detector 66. In an exemplary version of the invention, the ECG data is sampled once each millisecond at 16-bit resolution. The 150 Hz low-pass filter 76 and the slope detector 66 will be discussed in more detail below.

The 40 Hz filter defines the upper end of the passband for the monitor data output and is a multiple term finite-impulse-response (FIR) digital filter.

The output of the 40 Hz low-pass filter 50 is provided to two variable high-pass filters 52 and 54 connected in series. The output of the second variable high pass filter 54 is provided to the operator on the display 16. Both of the variable high-pass filters are single-pole high-pass digital filters and operate as described above, varying their respective corner frequencies according to a supplied coefficient "a." The manner in which the coefficient "a" is determined will be discussed below.

Although a single variable high-pass filter provides many benefits, it fails to solve a common problem faced by defibrillators. Immediately after a defibrillation discharge, the skin-electrode interface acquires a potential which is exponentially dissipated, taking about 5 to 10 seconds. For the sake of discussion, assume a linear decay of this voltage. The output of a single-pole high-pass filter approximates the derivative of its input. The derivative of a ramp is a slowly decaying value; thus the output of a single-pole high-pass filter receiving a linearly dissipating voltage is a slowly decaying DC value.

Thus, for 5 to 10 seconds after a defibrillation discharge, the patient's ECG waveform is superimposed upon a steady DC value. For high decay rates, the ECG waveform will be off-screen.

This DC value is typically substantial enough to negate the benefit of the variable high-pass filter. By providing two single-pole high-pass filters, the second filter will receive the DC output of the first and be able to eliminate the DC offset.

The coefficient "a" supplied to the two variable high-pass filters 52 and 54 is varied according to the DC offset output by the first variable high-pass filter 52. A higher DC offset results in a higher coefficient "a", increasing the corner frequency of the high-pass filters 52 and 54, allowing them to more quickly respond to the DC offset. As the DC offset decreases to zero, coefficient "a" can also effectively decrease to near zero, providing a highly accurate filter for stable ECG data signals.

However, only the output of the first high-pass filter 52 is used. To prevent the output of the second high-pass filter 54 from being away from the baseline when the output of the first high-pass filter 52 allows "a" to be reduced, the corner frequency of the second variable high-pass filter 54 is set to twice that of the first high-pass filter 52. This allows the output of the second high-pass filter to decay faster and thus be closer to the baseline than the output of the first high-pass filter 52.

The output of the first variable high-pass filter 52 is supplied to a 0.25 Hz low-pass filter 56, which provides an output essentially equal to the DC offset from the first variable high-pass filter 52. This filter is a single-pole low-pass digital filter as described above.

The absolute value 58 of the output from block 56 is supplied to a peak detector 60 having a delay. The peak detect allows the coefficient "a" to rise rapidly, and thus respond to large DC offsets quickly.

If the coefficient "a" were allowed to decrease as rapidly as the DC offset from the first variable high-pass filter 52, then as the DC offset neared zero, "a" would also near zero, effectively prolonging the ultimate elimination of the last bit of DC offset. Thus, the decay after a delay prohibits the coefficient "a" from decreasing until after the DC offset has reached zero.

The peak detector 60 uses two storage registers: "peak" and "decay." "Peak" stores a value representing the current peak in input values. "Decay" stores a value less than one which gets multiplied by the value in "peak," resulting in the output of the peak detector. The value in "decay" is decreased periodically to slowly decrease the output.

The output of the peak detector 60 is scaled such that, if it were passed directly to the first variable high-pass filter 52 as coefficient "a", a one milli-Volt output from the 0.25 low-pass filter 56 would result in a corner frequency of 0.25 Hz.

Figure 4:
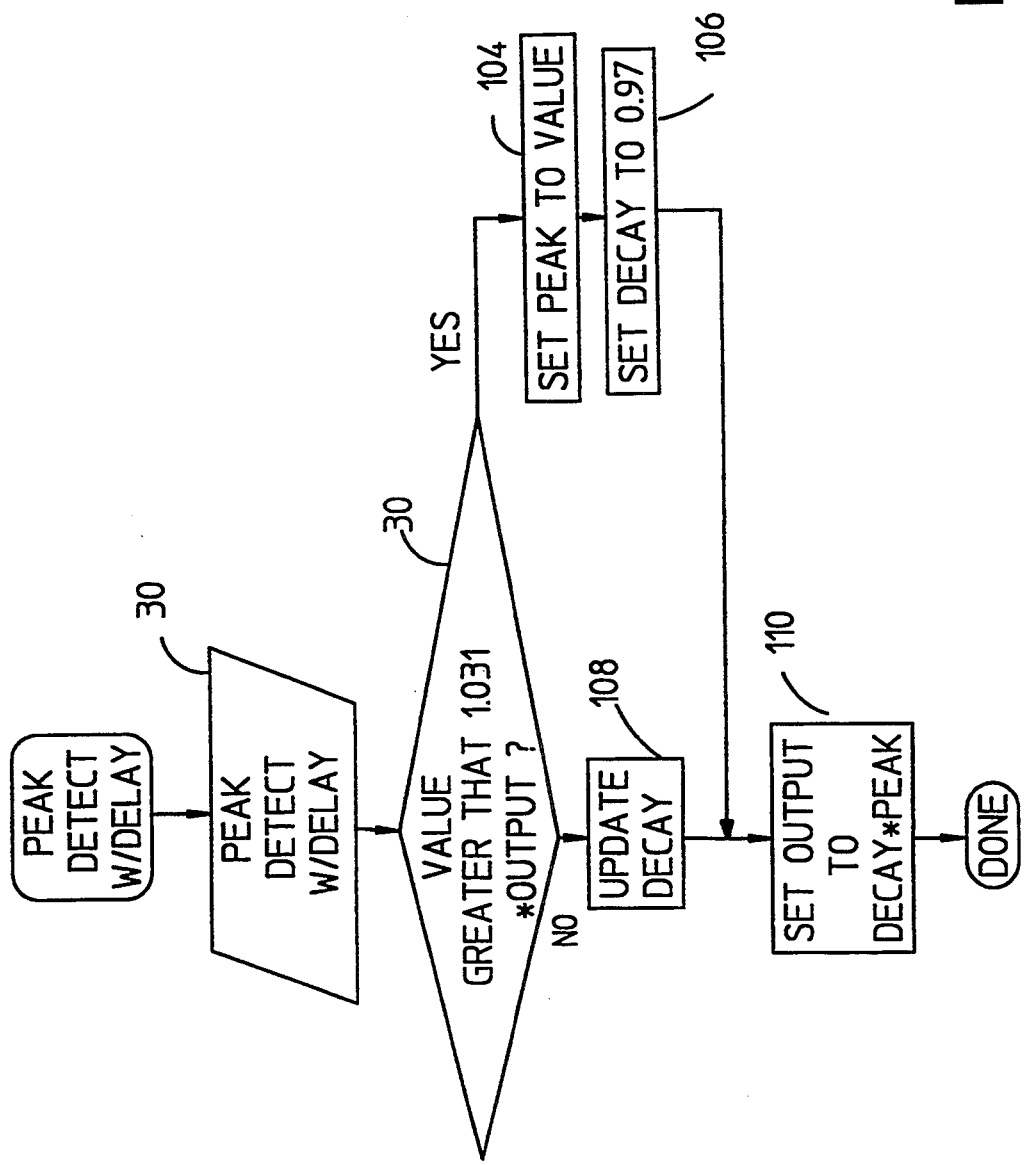
FIG. 4 shows a flow chart of a peak detect having decay.

Referring now to FIG. 4, every five milliseconds, the peak detector 60 gets 100 the next absolute value 58 of the low pass filter 56. If 102 the value is 3.1 percent greater than the peak detector's current output, then the value is stored 104 in the "peak" register and the value 0.97 is stored 106 in the "decay" register. The output is then equal to the product of the values stored in the "peak" and "decay" registers 110.

However, if 102 the value is not 3.1 percent greater than the peak detector's current output, then the value in the "decay" register is updated 108 according to the following equation.

$$decay(n+1) = decay(n) - 0.0045(1 - decay(n)) \qquad (6)$$

As the value in the "decay" register decreases, its rate of decrease becomes greater. Equation 6 can be solved for decay(n) yielding:

$$decay(n) = 1 - (1 - decay(0))(1 + 0.0045)^n. \qquad (7)$$

Thus, the value stored in the "decay" register, assuming no new peak is detected in block 102, will decay as shown in the following table.

TABLE 1

| n | SECONDS | "DECAY" REGISTER |
|---|---------|------------------|
| 268 | 1.34 | 0.90 |
| 422 | 2.11 | 0.80 |
| 512 | 2.56 | 0.70 |
| 626 | 3.13 | 0.50 |
| 716 | 3.58 | 0.25 |
| 780 | 3.90 | 0.00 |

Referring again to FIG. 3, the output of the peak detector 60 is provided to a variable attenuator 62, which for the present will be described as passing the output of the peak detector 60 on to the clipper 64. The description of the variable attenuator 62 will be augmented below.

The clipper 64 provides as its output the greater of (1) the output of the variable attenuator 62, and (2) a coefficient "a" corresponding to a corner frequency of 0.025 Hz for the first variable high-pass filter 52. Thus, the minimum corner frequency for the first variable high-pass filter 52 is 0.025 Hz and for the second variable high-pass filter 54 is 0.050 Hz.

The coefficient "a" to the first and second variable high-pass filters 52, 54 can also be varied by the "activity" of the input ECG data signal.

A digital triangular convolution filter operates on the input ECG data and provides as an output a "slope" Z which corresponds to the average slope of the last 40 ms of ECG data. For this reason, the digital triangular convolution filter is termed herein as a "slope detector" 66. When the ECG signal has high activity, such as during the QRS complex, the output of the slope detector will be elevated. When the ECG signal is essentially flat, the output of the slope detector will be zero.

The slope detector's coefficients are selected such that its output slope is the average slope of the last 40 ms of the ECG data. An exemplary equation used by the slope detector 66 on ECG data sampled at 5 ms intervals is given in the following equation.

$$Z(t) = \{-32X[-7] - 29X[-6] - 20X[-5]$$
$$-7X[-4] + 7X[-3] + 20X[-2]$$
$$+29X[-1] + 32X[0]\}/64 \qquad (8)$$

An activity detector 68 receives the slope Z from the slope detector 66 and provides as an output a signal which is the average of the absolute values of the last four slopes.

$$Y[0] = \frac{|Z[0]| + |Z[-1]| + |Z[-2]| + |Z[-3]|}{4} \qquad (9)$$

The output of the slope detector 68 cannot be used directly because its output can drop near zero when the slope of the input ECG signal changes signs. This will occur at the peak of each R wave. Other equations for an activity detector can be used. The requirements are that the activity Y[0] remain high for periods of increased activity in the ECG data.

A threshold detector 70 low-pass filters the output of the activity detector 68 with a corner frequency of 0.1 Hz. Thus, the output of the threshold detector is the near-DC component of the slope of the input ECG data, and serves as a threshold for altering the coefficient "a." The threshold detector is a single-pole low-pass digital filter with a corner frequency of 0.1 Hz, implemented as described above.

Block 72 takes the ratio of threshold to activity, and supplies it to a clipper 74. If the ratio is greater than one, then the activity is less than the threshold, and no modification of "a" will occur as a result of the ECG activity.

However, if the ratio is less than one, then the activity is greater than the threshold and the ECG signal is in a period of increased activity. Thus, the passband of the variable high-pass filters 52, 54 should be decreased to decrease the QRS signal's effect on the filter's accumulated amounts w.

The variable attenuator takes the output of the peak detector 60 and multiplies it by the output of the clipper 74. Above, to keep the discussion of varying the coefficient "a" based on the DC offset of the filters 52 and 54 simple, the variable attenuator was described as passing the output of the peak detector 60 directly to the clipper 64. During periods of low ECG activity, the output of clipper 74 will be one, and the simplified description is correct.

However, during times of high ECG activity, that is, the output of clipper 74 is less than one, the output of the variable attenuator will be decreased by the ratio of threshold to activity as provided by block 72. This has the effect of decreasing the coefficient "a" supplied to the first and second variable high-pass filters 52 and 54 during times of increased ECG activity.

The 150 Hz low-pass filter 76 mentioned above defines the upper end of the passband for the diagnostic data output and is a multiple term finite-impulse-response (FIR) digital filter.

The output of the 150 Hz low-pass filter 76 is provided to a third and fourth variable high-pass filters 78 and 80 connected in series. The diagnostic output of the fourth variable high-pass filter 80 is provided to the user. Thus, their primary purpose is to maintain the ECG signal with the lowest possible corner frequency of high-pass filtering.

The third and fourth variable high-pass filters 78, 80 are single-pole high-pass digital filters and operate as described above. They both operate with the same corner frequency, unlike the first and second variable high-pass filters 52 and 54 discussed above in reference to the monitor data output.

The output of the 150 Hz low-pass filter is also provided to a 2 Hz single-pole high-pass digital filter 82. The 2 Hz corner frequency is set so that the filter's output contains virtually no baseline wander.

The output of the 2 Hz high-pass filter 82 is subtracted 84, 86 from the outputs of the third and fourth variable high-pass filters 78, 80. The resulting differences are bandpass filters having passbands between 2 Hz and the corner frequencies of the third and fourth variable high-pass filters 78, 80. The maximum of the absolute values of the two differences is provided to block 90 by block 88.

Block 90 scales the output of block 88 to the gain of the ECG display 16 (FIG. 1). It does this by dividing the output of block 88 by the voltage which represents the extreme edge of the output device, such as the paper edge 24 of the strip recorder 22, and squaring the result. The output of block 90 is provided to a peak detector 91. The peak detector provides an output to the third and fourth variable high-pass filters 78, 80 through a second variable attenuator 92 and clipper 94.

Figure 5:
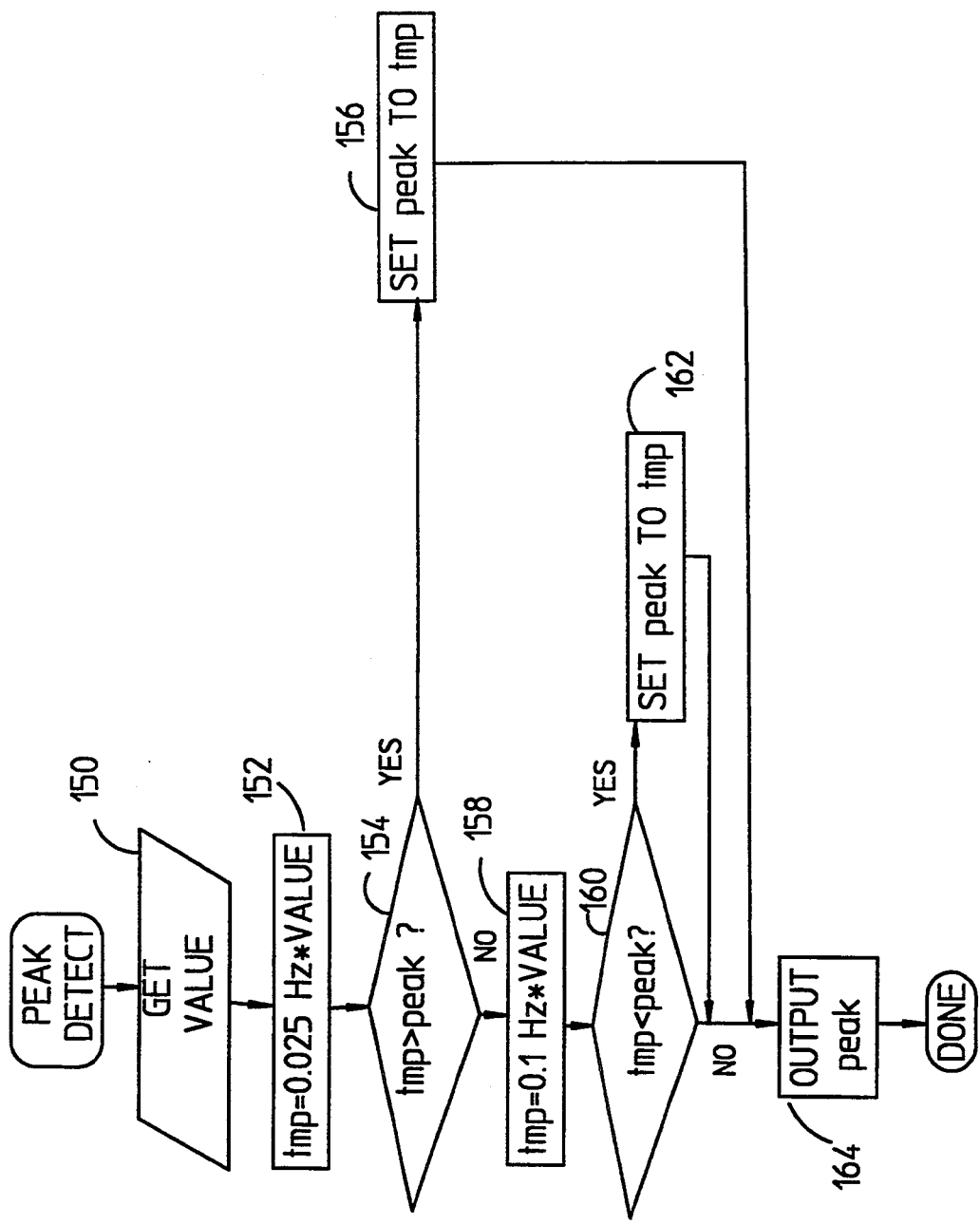
FIG. 5 shows a flow chart of a second peak detect.

Referring now to FIG. 5, the peak detector 91 uses a storage register "peak" for storing peak values detected in the output of block 90. As a first step, the peak detector 91 gets 150 the output of block 90.

That output is scaled 152 such that an output of unity from block 90 would result in a corner frequency of 0.025 Hz at variable high-pass filters 78, 80. If 154 the resulting scaled value "tmp" is greater than the value stored in "peak," then the value in "tmp" is stored in "peak" and provided 164 as the output of the peak detector 91.

However, if 154 the resulting scaled value "tmp" is less than the values stored in "peak," then the output of block 90 is scaled 158 such that an output of unity from block 90 would result in a corner frequency of 0.10 Hz. If 160 the resulting scaled value "tmp" is less than the value stored in "peak," then the value in "tmp" is stored in "peak" and provided 164 as the output of the peak detector 91.

Thus, the output from the peak detector 91 changes in response to two different conditions. If the output from block 88 is so large that it would exceed the current peak value, then the peak detector's output changes to increase the corner frequency of the variable high-pass filters 78, 80. If the output from block 88 is so small that four times its value does not exceed the current peak value, then the peak detector's output changes to decrease the corner frequency of the variable high-pass filters 78, 80.

The second variable attenuator 92 operates similarly to the first variable attenuator 62. It takes the output of block 91 and multiplies it by the output of the clipper 74. During periods of low ECG activity, the output of the clipper 74 will be one, and thus the output of the second variable attenuator will equal the output of block 91. Otherwise, the output of the second variable attenuator will be decreased proportionally to the ratio of the output of the threshold detector 70 to the output of the activity detector 68.

The output of the second variable attenuator is clipped such that the resultant "a" supplied to the third and fourth variable high-pass filters 78 and 80 results in corner frequency of 0.025 Hz.

A further refinement in the control of coefficient "a" is preferred. As described above, the accumulated value w in a single-pole filter tracks the low-frequency components of the input signal x.

During times of high activity in the ECG signal, the activity detector 68 causes rapid reductions in the coefficient "a" through the actions of the first and second variable attenuators 62 and 92, thereby preventing w from being affected by the QRS complex. This reduction in coefficient "a" also prevents w from accurately tracking any low-frequency baseline wander present, thereby affecting the appearance of the signals at the outputs of the variable high-pass filters 54 and 80.

By continuing to change the accumulated amount w during times of high activity at the same rate as it was changing just before activity occurred, the accumulated amount w will more accurately track baseline wander. This can be accomplished by varying the manner in which the accumulated amount is updated.

Let "$a_1$" be the coefficient "a" after being reduced by QRS activity in the variable attenuators 62 and 92 and let "$a_2$" be the difference between the two: $a - a_1$. Finally, let "slope" be $w[n] - w[n-1]$ where n represents the sample time at which the output of block 72 is one, that is, the last sample at which "a" was not diminished by QRS activity. Then the accumulated amount w can maintain a constant rate of change during times of high QRS activity according to the following equation.

$$w[0] = w[-1] + a_1 y[-1] + (a_2/a) \text{slope} \tag{10}$$

Figure 6:
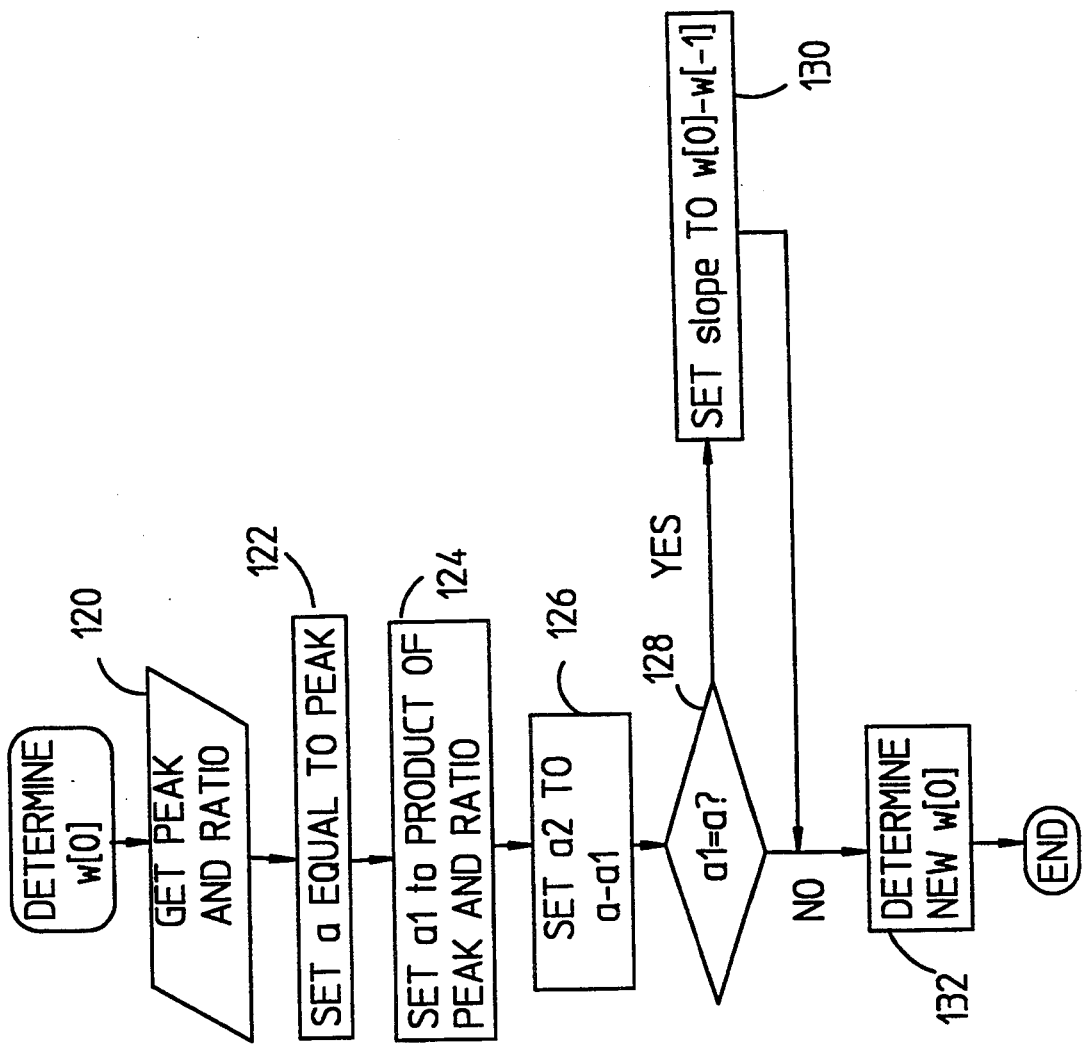
FIG. 6 shows a flow chart of a method for determining an accumulated amount w.

Referring now to FIG. 6, a flow chart of the above refinement is shown. The outputs of the peak detector 60 and the clipped ratio from clipper 74 are read 120. Coefficient "a" is set 122 to the output of the peak detector and "$a_1$" is set 124 to the product of the two read values. Value $a_2$ is set to the difference between "a" and "$a_1$." If 128 that difference is zero, then it is not a time of high QRS activity and slope is updated 130. Then w[0] is determined according to equation (10), given above.

Although the present invention has been described in considerable detail with reference to certain preferred versions and values, other versions are possible.

The described version uses two variable high-pass filters in series 52, 54, and 78, 80 to eliminate the effects of a constant slope in the offset signal superimposed on the ECG signal. As a baseline wander filter according to the present invention has uses in devices other than a defibrillator, a single variable high-pass filter may be used.

The described version changes the corner frequency of the variable high-pass filters 52, 54, 78, 80 according to both the DC offset of the input ECG data and the QRS activity. A variable high-pass filter according to the present invention may be built which varies its corner frequency according to either DC offset, or QRS activity, or both.

Therefore, the spirit and scope of the appended claims should not be limited to the description of the preferred versions contained herein.

What is claimed is:

1. A method for accurately displaying an ECG signal, comprising the steps of:

receiving ECG input data;

filtering said ECG input data with a high pass filter having a variable corner frequency, thereby creating an ECG signal;

detecting the presence of a QRS event in said ECG input data;

in response to said detecting the presence of a QRS event step, decreasing said variable corner frequency of said high pass filter; and displaying said ECG signal.

2. The method of claim 1, further comprising the steps of:

detecting the presence of a DC offset caused by a defibrillation discharge in said ECG input data; and in response to said detecting the presence of a DC offset step, increasing said variable corner frequency of said high pass filter.

3. An apparatus for accurately displaying an ECG signal, comprising:

a high pass filter having an input, an output, and a variable corner frequency, wherein the input of said high pass filter is for connection to ECG input data, and wherein the output of said high pass filter is for connection to a display device, said display device for displaying said ECG signal;

first detection circuitry for detecting the presence of a QRS event in said ECG input data; and attenuation circuitry for decreasing said first variable corner frequency of said high pass filter in response to said first detection circuitry detecting the presence of a QRS event.

4. The apparatus of claim 3, further comprising:

second detection circuitry for detecting the presence of a DC offset caused by a defibrillation discharge in said ECG input data; and said attenuation circuitry also for increasing said variable corner frequency of said high pass filter in response to said second detection circuitry detecting the presence of said DC offset.

5. An apparatus for accurately displaying an ECG signal, comprising:

a first high pass filter having an input, an output, and a first variable corner frequency, wherein the input of said first high pass filter is for connection to ECG input data;

a second high pass filter having an input, an output, and a second variable corner frequency, wherein the input of said second high pass filter is connected to the output of said first high pass filter and wherein the output of said second high pass filter is for connection to a display device, said display device for displaying said ECG signal;

first detection circuitry for detecting the presence of a QRS event in said ECG input data; and attenuation circuitry for decreasing said first and second variable corner frequencies of said first and second high pass filters in response to said first detection circuitry detecting the presence of a QRS event.

6. The apparatus of claim 5, further comprising:

second detection circuitry for detecting the presence of a DC offset caused by a defibrillation discharge in said ECG input data; and said attenuation circuitry also for increasing said first and second variable corner frequencies of said first and second high pass filters in response to said second detection circuitry detecting the presence of said DC offset.

7. The apparatus of claim 6, wherein said second variable corner frequency is larger than said first variable corner frequency.

8. The apparatus of claim 6, wherein said second variable corner frequency is approximately twice as large as said first variable corner frequency.

* * * * *